United States Patent
Shuck

(10) Patent No.: US 7,150,999 B1
(45) Date of Patent: Dec. 19, 2006

(54) PROCESS FOR FILLING MICROFLUIDIC CHANNELS

(75) Inventor: Gary L. Shuck, Fremont, CA (US)

(73) Assignee: Califer Life Sciences, Inc., Mountain View, CA (US)

( * ) Notice: Subject to any disclaimer, the term of this patent is extended or adjusted under 35 U.S.C. 154(b) by 588 days.

(21) Appl. No.: 10/092,011

(22) Filed: Mar. 5, 2002

Related U.S. Application Data

(60) Provisional application No. 60/274,478, filed on Mar. 9, 2001.

(51) Int. Cl.
*G01N 1/10* (2006.01)

(52) U.S. Cl. .................. 436/180; 422/99; 422/100; 422/101

(58) Field of Classification Search .......... 422/99–101; 435/254.1; 436/180; 438/126
See application file for complete search history.

(56) References Cited

U.S. PATENT DOCUMENTS

| | | | |
|---|---|---|---|
| 4,390,403 A | | 6/1983 | Batchelder |
| 4,537,231 A | * | 8/1985 | Hasskamp ............ 141/238 |
| 4,908,112 A | | 3/1990 | Pace |
| 5,126,022 A | | 6/1992 | Soane et al. |
| 5,498,392 A | | 3/1996 | Wilding et al. |
| 5,571,410 A | * | 11/1996 | Swedberg et al. ....... 210/198.2 |
| 5,585,069 A | | 12/1996 | Zanzucchi et al. |
| 5,593,838 A | | 1/1997 | Zanzucchi et al. |
| 5,603,351 A | | 2/1997 | Cherukuri et al. |
| 5,635,358 A | | 6/1997 | Wilding et al. |
| 5,637,469 A | | 6/1997 | Wilding et al. |
| 5,699,157 A | | 12/1997 | Parce |
| 5,716,852 A | | 2/1998 | Yager et al. |
| 5,750,015 A | | 5/1998 | Soane et al. |
| 5,779,868 A | | 7/1998 | Parce et al. |
| 5,800,690 A | | 9/1998 | Chow et al. |
| 5,858,187 A | | 1/1999 | Ramsey et al. |
| 5,858,195 A | | 1/1999 | Ramsey |
| 5,866,442 A | * | 2/1999 | Brand ................ 438/108 |
| 5,869,004 A | | 2/1999 | Parce et al. |
| 5,876,675 A | | 3/1999 | Kennedy |
| 5,880,071 A | | 3/1999 | Parce et al. |
| 5,882,465 A | | 3/1999 | McReynolds |
| 5,885,470 A | | 3/1999 | Parce et al. |
| 5,932,100 A | | 8/1999 | Yager et al. |
| 5,942,443 A | | 8/1999 | Parce et al. |
| 5,948,227 A | | 9/1999 | Dubrow |
| 5,955,028 A | | 9/1999 | Chow |

(Continued)

FOREIGN PATENT DOCUMENTS

| | | |
|---|---|---|
| WO | WO 9604547 | 2/1996 |

(Continued)

OTHER PUBLICATIONS

Dasgupta, P.K. et al., "Electroosmosis: A Reliable Fluid Propulsion System for Flow Injection Analysis," *Anal. Chem.* (1994) 66:1792-1798.

(Continued)

*Primary Examiner*—Jill Warden
*Assistant Examiner*—Jyoti Nagpaul
(74) *Attorney, Agent, or Firm*—Donald R. McKenna, Ph.D; Ann C. Petersen

(57) ABSTRACT

The present invention provides novel methods and devices for filling at least one microfluidic channel with a gas or with a degassed fluid. In particular the methods and devices of the invention are useful in completely filling substantially all areas of a microfluidic device with a gas or with a degassed fluid without incorporating bubbles within such microfluidic devices.

22 Claims, 4 Drawing Sheets

U.S. PATENT DOCUMENTS

| | | | |
|---|---|---|---|
| 5,958,694 | A | 9/1999 | Nikiforov |
| 5,959,291 | A | 9/1999 | Jensen |
| 5,965,410 | A | 10/1999 | Chow et al. |
| 5,976,336 | A | 11/1999 | Dubrow et al. |
| 5,989,402 | A | 11/1999 | Chow et al. |
| 6,001,229 | A | 12/1999 | Ramsey |
| 6,001,231 | A | 12/1999 | Kopf-Sill |
| 6,012,902 | A | 1/2000 | Parce |
| 6,042,709 | A | 3/2000 | Parce et al. |
| 6,046,076 | A * | 4/2000 | Mitchell et al. ............ 438/127 |
| 6,062,261 | A | 5/2000 | Jacobson et al. |
| 6,074,725 | A | 6/2000 | Kennedy |
| 6,100,541 | A | 8/2000 | Nagle et al. |
| 6,119,895 | A * | 9/2000 | Fugere et al. ................... 222/1 |
| 6,120,666 | A | 9/2000 | Jacobson et al. |
| 6,120,985 | A * | 9/2000 | Laugharn et al. ............ 435/1.3 |
| 6,149,787 | A | 11/2000 | Chow et al. |
| 6,221,226 | B1 | 4/2001 | Kopf-Sill |
| 6,235,471 | B1 | 5/2001 | Knapp et al. |
| 6,255,142 | B1 * | 7/2001 | Babiarz et al. ............. 438/126 |
| 6,280,589 | B1 | 8/2001 | Manz et al. |

FOREIGN PATENT DOCUMENTS

| | | |
|---|---|---|
| WO | WO 9702357 | 1/1997 |
| WO | WO 9845481 | 10/1998 |

OTHER PUBLICATIONS

Effenhauser, C.S. et al., "Glass Chips for High-Speed Capillary Electrophoresis Separations with Submicrometer Plate Heights," *Anal. Chem.* (1993) 65: 2637-2642.

Effenhauser, C.S. et al., "High Speed Separation of Anitsense Oligonucleotides on a Micromachined Capillary Electrophoresis Device," *Anal. Chem.* (1994) 66: 2949-2953.

Effenhauser, C.S. et al., "Integrated Capillary Electrophoresis on Flexible Silicone Microdevices: Analysis of DNA Restriction Fragments and Detection of Single DNA Molecules on Microchips," *Anal. Chem.* (1997) 69: 3451-3457.

Fan, Z.H. et al., "Micromachining of Capillary Electrophoresis Injectors and Separators on Glass Chips and Evaluation of Flow at Capillary Intersections," *Anal. Chem.* (1994) 66: 177-184.

Fister, J.C. III et al., "Counting Single Chromophore Molecules for Ultrasensitive Analysis and Separations on Microchip Devices," *Anal. Chem.* (1998) 70: 431-437.

Hadd, A.G. et al., "Microfluidic Assays of Acetylcholinesterase," *Anal. Chem.* (1999) 71: 5206-5212.

Harrison, J. et al., "Capillary Electrophoresis and Sample Injection Systems Integrated on a Planar Glass Chip," *Anal. Chem.* (1992) 64: 1926-1932.

Harrison, J. et al., "Towards Miniaturized Electrophoresis and Chemical Analysis Systems on Silicon: An Alternative to Chemical Sensors*," *Sensors and Actuators B* (1993) 10: 107-116.

Harrison, J. et al., "Micromachining a Miniaturized Capillary Electrophoresis-Based Chemical Analysis System on a Chip," *Science* (1993) 261: 895-897.

Harrison, D.J. et al., "Integrated Electrophoresis Systems for Biochemical Analyses," *Solid-State Sensor and Actuator Workshop* (1994) 21-24.

Jacobson, S.C. et al., "Effects of Injection Schemes and Column Geometry on the Performance of Microchip Electrophoresis Devices," *Anal. Chem.* (1994) 66:1107-1113.

Jacobson, S.C. et al., "High-Speed Separations on a Microchip," *Anal. Chem.* (1994) 66: 1114-1118.

Jacobson, S.C. et al., "Open Channel Electrochromatography on a Microchip," *Anal. Chem.* (1994) 66: 2369-2373.

Jacobson, S.C. et al., "Precolumn Reactions with Electrophoretic Analysis Integrated on a Microchip," *Anal. Chem.* (1994) 66: 4127-4132.

Jacobson, S.C. et al., "Microchip Electrophoresis with Sample Stacking," *Electrophoresis* (1995) 16: 481-486.

Jacobson, S.C. et al., "Fused Quartz Substrates for Microchip Electrophoresis," *Anal. Chem.* (1995) 67: 2059-2063.

Jacobson, S.C. et al., "Integrated Microdevice for DNA Restriction Fragment Analysis," *Anal. Chem.* (1996) 68: 720-723.

Jacobson, S.C. et al., "Electrokinetic Focusing in Microfabricated Channel Structures," *Anal. Chem.* (1997) 69: 3212-3217.

Jacobson, S.C. et al., "Microfluidic Devices for Electronkinetically Driven Parallel and Serial Mixing," *Anal. Chem.* (1999) 71: 4455-4459.

Manz, A. et al., "Miniaturized Total Chemical Analysis Systems: a Novel Concept for Chemical Sensing," *Sensors and Actuators* (1990) B1: 244-248.

Manz, A. et al., "Micromachining of Monocrystalline Silicon and Glass for Chemical Analysis Systems," *Trends in Analytical Chemistry* (1991) 10:144-149.

Manz, A. et al., "Planar Chips Technology for Miniaturization and Integration of Separation Techniques into Monitoring Systems," *Journal of Chromatography* (1992) 593:253-258.

Manz, A. et al., "Planar Chips Technology for Miniaturization of Separation Systems: A Developing Perspective in Chemical Monitoring."

Manz, A. et al., "Electroosmotic Pumping and Electrophoretic Separations for Miniaturized Chemical Analysis Systems," J. Micromach. Microeng. (1994) 4: 257-265.

Manz, A. et al., "Parallel Capillaries for High Throughput in Electrophoretic Separations and Electroosmotic Drug Discovery Systems," International Conference on Solid-State Sensors and Actuators (1997) 915-918.

McCormick, R.M. et al., "Microchannel Electrophoretic Separations of DNA in Injection-Molded Plastic Substrates," *Anal. Chem.* (1997) 69: 2626-2630.

Moore, A.W. et al., "Microchip Separations of Neutral Species via Micellar Electronkinetic Capillary Chromatography," *Anal. Chem.* (1995) 67: 4184-4189.

Ramsey, J.M. et al., "Microfabricated Chemical Measurement Systems," *Nature Medicine* (1995) 1:1093-1096.

Salimi-Moosavi, H. et al., "Biology Lab-on-a-Chip for Drug Screening," Solid-State Sensor and Actuator Workshop (1998) 350-353.

Seiler, K. et al., "Planar Glass Chips for Capillary Electrophoresis: Repetitive Sample Injection, Quantitation, and Separation Efficiency," *Anal. Chem.* (1993) 65:1481-1488.

Seiler, K. et al., "Electroosmotic Pumping and Valveless Control of Fluid Flow within a Manifold of Capillaries on a Glass Chip," *Anal. Chem.* (1994) 66:3485-3491.

Ueda, M. et al., "Imaging of a Band for DNA Fragment Migrating in Microchannel on Integrated Microchip," *Materials Science and Engineering C* (2000) 12:33-36.

Wang, C. et al., "Integration of Immobilized Trypsin Bead Beds for Protein Degestion within a Microfluidic Chip Incorporating Capillary Electrophoresis Separations and an Electrospray Mass Spectrometry Interface," *Rapid Commin. Mass Spectrom.* (2000) 14:1377-1383.

Woolley, A.T. et al., "Ultra-High-Speed DNA Fragment Separations Using Microfabricated Capillary Array Electrophoresis Chips," *Proc. Natl. Acad. Sci. USA* (1994) 91:11348-11352.

Woolley, A.T. et al., "Functional Integration of PCR Amplification and Capillary Electrophoresis in a Microfabricated DNA Analysis Device," Anal. Chem. (1996) 68: 4081-4086.

Woolley, A.T. et al., "High-Speed DNA Genotyping Using Microfabricated Capillary Array Electrophoresis Chips," *Anal. Chem.* (1997) 69:2181-2186.

Woolley, A.T. et al., "Capillary Electrophoresis Chips with Integrated Electrochemical Detection," *Anal. Chem.* (1998) 70: 684-688.

Zhang, B. et al., "Microfabricated Devices for Capillary Electrophoresis-Electrospray Mass Spectrometry," *Anal. Chem.* (1999) 71:3258-3264.

* cited by examiner

PROCESS FOR FILLING MICROFLUIDIC CHANNELS

CROSS REFERENCE TO RELATED APPLICATION

This application is related to U.S. Provisional Patent Application No. 60/274,478, filed Mar. 9, 2001, which is incorporated herein by reference in its entirety for all purposes.

BACKGROUND OF THE INVENTION

The performance of chemical or biochemical analyses, assays, syntheses or preparations often requires a large number of separate manipulations to be performed on the material(s) or component(s) to be assayed, including measuring, aliquotting, transferring, diluting, mixing, separating, detecting, incubating, etc. Microfluidic technology miniaturizes these manipulations and integrates them so that they can be executed within one or a few microfluidic devices. For example, pioneering microfluidic methods of performing biological assays in microfluidic systems have been developed, such as those described by Parce et al., "High Throughput Screening Assay Systems in Microscale Fluidic Devices" U.S. Pat. No. 5,942,443 and Knapp et al., "Closed Loop Biochemical Analyzers" (WO 98/45481).

Many examples of microfluidic devices incorporate capillary or other similar elements extending from body structures of the devices. See, e.g., U.S. Pat. No. 6,149,787, issued Nov. 21, 2000, entitled "External Material Accession Systems and Methods," to A. Chow et al., for an illustration of one possible microfluidic device incorporating capillary elements. Typically, a capillary element, which includes a capillary channel disposed therethrough, provides fluid communication between, e.g., a microchannel, microreservoir, microchannel network, or other similar cavity or element housed within the body structure of a microfluidic device and a fluid source outside of the microfluidic device. Such capillary elements are optionally used to load reagents, samples, or other materials from external sources, such as microwell plates, into the microfluidic device (or more specifically into desired microchannels, etc.).

Typically, as part of the preparation and/or manufacture of microfluidic devices, the microfluidic elements (e.g., microchannels, capillary elements, etc). are often filled and wetted with a desired gas, or more typically, a desired fluid, before the specific assays, etc. for which the microfluidic device was designed, are performed. One concern associated with the pre-filling of microfluidic devices containing capillary elements is the possibility of bubbles (of air or other gasses) being trapped within the junction or area where the capillary element joins/abuts the substrate layers of the microfluidic device. This is especially true with increasingly small junction areas. Bubbles can also be of concern in the pre-filling of microfluidic devices that have complex or intricate combinations of microfluidic elements (e.g., microchannels, etc.). For example, initial filling of microchannels containing large changes in cross-sectional area can present regions wherein bubbles (or other incomplete pre-filling problems) can be of concern.

A welcome addition to the art would be the ability to pre-fill microfluidic devices containing such capillary elements and complex/intricate microfluidic element configurations in microfluidic devices without the concern of bubbles being trapped in the interface between the capillary element and the substrate layer(s) of the microfluidic device or within the microfluidic elements of the device. The present invention includes methods and devices that accomplish these objectives.

BRIEF SUMMARY OF THE INVENTION

The present invention provides methods, systems, kits, and devices for filling microfluidic channels with a gas and/or with a degassed fluid. The microfluidic channel(s) is placed under a total or partial vacuum, thus becoming either totally or partially evacuated. This produces a first pressure internally. The totally or partially evacuated microfluidic channel is then submerged in a gas or a degassed fluid that is at a higher pressure than the totally or partially evacuated microfluidic channel. After being submerged, the microfluidic channel(s) is vented to the gas or degassed fluid in which it is submerged, thus allowing the gas or degassed fluid to fill the totally or partially evacuated microfluidic channel(s).

In one aspect of the invention, a method of filling at least one microfluidic element of a microfluidic device with a gas or fluid is disclosed which comprises placing the microfluidic device in a vacuum chamber, applying a vacuum to the vacuum chamber, introducing the gas or fluid into the vacuum chamber while the microfluidic device remains under vacuum so that the microfluidic device is submerged in the gas or fluid, venting the at least one microfluidic element to the fluid, and filling the at least one microfluidic element with the gas or fluid. The vacuum applied to the vacuum chamber can range from between about 0 and 102 kPa, for example, from between about 15 and 85 kPa, from between about 30 and 70 kPa, from between about 45 and 55 kPa, and from between about 0 and 5 kPa, for example. The step of filling the at least one microfluidic element with a gas or fluid can comprise, for example, filling the at least one microfluidic element with at least one fluid selected from the group comprising water, buffer, EDTA solution, DMSO, PEG, polyacrylamide, and NaOH solution, or at least one inert gas, such as carbon dioxide or nitrogen, or a combination of any one or more of the fluids and gases.

In another aspect of the invention, a method of preparing at least one microfluidic device for a gas or fluid-filling operation is disclosed which comprises placing the at least one microfluidic device in a vacuum chamber and applying a vacuum to the vacuum chamber. The method can comprise placing two or more microfluidic devices in the vacuum chamber. The method may then include introducing at least one of a gas or a fluid into the vacuum chamber while the at least one microfluidic device remains under vacuum. The method may comprise introducing both at least one gas and at least one fluid into the vacuum chamber. The at least one gas can be introduced into the vacuum chamber before introducing the at least one fluid into the vacuum chamber.

In yet another aspect of the invention, a system for filling a microfluidic device with a gas or a fluid is disclosed which comprises a chamber configured to receive the microfluidic device, a vacuum source which is fluidly coupled to the chamber and which is configured to apply a vacuum to the chamber, and at least one source of a gas or fluid which is fluidly coupled to the chamber and which is configured to introduce at least one of a gas or a fluid into the chamber. The system may further include a detector which is configured to monitor filling of the microfluidic device with the gas or fluid. The system may also include a processor which is operably coupled to the microfluidic device, and which comprises an instruction set for acquiring data from the detector and for controlling filling of the microfluidic device with the gas or the fluid.

In some aspects, the invention comprises a method of filling at least one microfluidic channel. Such method of filling comprises placing the at least one microfluidic channel under a total or partial vacuum, thereby producing a substantially evacuated at least one microfluidic channel having a first pressure internally; submerging the substantially evacuated at least one microfluidic channel in a gas or in a degassed fluid which has a second pressure that is greater than the first pressure (i.e., the pressure of the gas or degassed fluid is greater than the pressure within the submerged substantially evacuated at least one microfluidic channel), thereby producing a submerged substantially evacuated at least one microfluidic channel; and venting the submerged substantially evacuated at least one microfluidic channel to the gas or degassed fluid, thereby filling the submerged substantially evacuated at least one microfluidic channel with the gas or with the degassed fluid and producing a fluid-fill or a gas-filled at least one microfluidic channel.

In other aspects the invention optionally comprises submerging the substantially evacuated at least one microfluidic channel in a degassed fluid comprising a buffer. Other aspects of the invention optionally comprise submerging the substantially evacuated at least one microfluidic channel in water, an EDTA solution, DMSO, PEG, polyacrylamide, an NaOH solution, or the like. Additionally, the invention optionally comprises diffusing a fluid into a gas-filled at least one microfluidic channel. In some aspects of the invention, the gas in which the at least one microfluidic channel is submerged optionally comprises an inert gas, $CO_2$, $N_2$, or the like.

In yet other aspects, the at least one microfluidic channel is optionally fluidly connected to at least one capillary element (which includes a capillary channel disposed within the capillary element). Furthermore, the at least one microfluidic channel of the invention optionally comprises a plurality of microfluidic channels or further comprises one or more micro-reservoir or microchamber.

The total or partial vacuum under which the at least one microfluidic channel is placed, in various aspects of the invention, optionally comprises from between at least about 0.5 kPa to at least about 102 kPa or more, between at least about 15 kPa to at least about 85 kPa or more, between at least about 30 kPa to at least about 70 kPa or more, or between at least 45 kPa to at least about 55 kPa or more. In preferred embodiments, the at least one microfluidic channel optionally is placed under between at least about 0.5 kPa to at least about 5 kPa or more total or partial vacuum.

Additionally, the invention comprises a device or system for filling a microfluidic device (e.g., one that comprises at least one microfluidic channel) with a gas or a degassed fluid. In various aspects the device for filling comprises a chamber configured to receive the microfluidic device, a vacuum system configured to evacuate atmospheric gasses from the chamber, and a system configured to add the gas or degassed fluid into the chamber.

Optionally, the device for filling can further comprise a system for venting the at least one microfluidic channel to the chamber in which the microfluidic device is placed. Furthermore, the invention optionally comprises a detector system that is configured to monitor the filling of the microfluidic device with the gas or the degassed fluid. In yet other aspects the invention optionally comprises a computer operably coupled to the device for filling a microfluidic device, wherein the computer comprises an instruction set for acquiring data from the detector and for controlling the filling of the microfluidic device with the gas or the degassed fluid. Many additional aspects of the invention will be apparent upon complete review of this disclosure, including uses of the devices and systems of the invention, methods of manufacture of the devices and systems of the invention, kits for practicing the methods of the invention and the like. For example, kits comprising any of the devices or systems set forth above, or elements thereof, in conjunction with, e.g., packaging materials (e.g., containers, sealable plastic bags, etc.) and instructions for using the devices, e.g., to practice the methods herein, are also contemplated.

DETAILED DESCRIPTION

Figure 1:
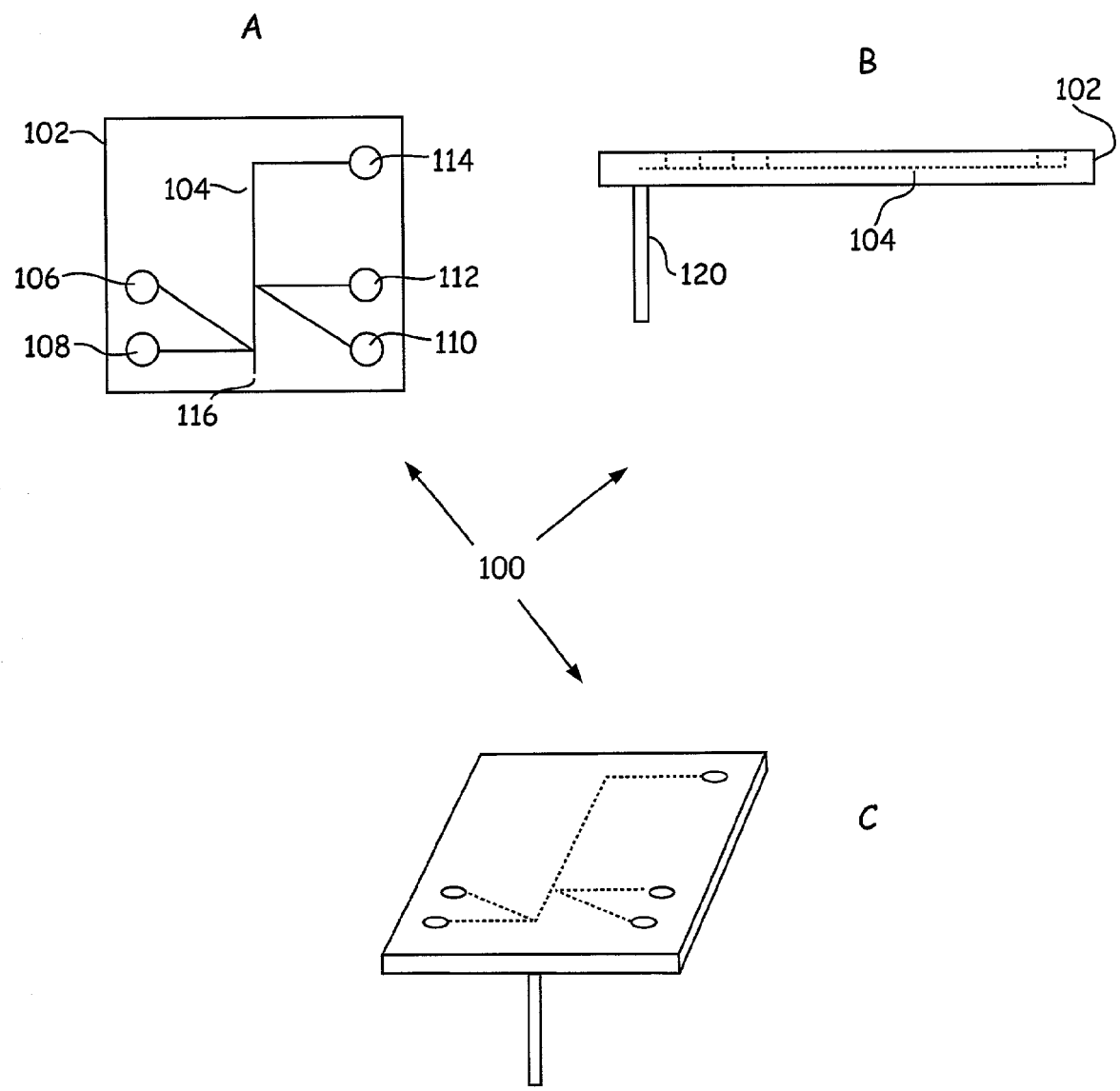
FIG. 1, panels A, B, and C comprises schematic top and side views of an example microfluidic device (including a capillary element) capable of being evacuated and filled through the methods and devices of the invention.

The methods and devices of the invention directly address and solve concerns associated with the filling (i.e., pre-filling done before any assays, etc. are performed) of micro fluidic channels and devices. Specifically, the invention provides methods for substantially evacuating gas(ses) from microfluidic channels and microfluidic devices and subsequently filling the microfluidic channels and devices with desired gasses and/or fluids. As used herein, the term "filling" in relation to the methods and devices of this invention more specifically refers to the pre-filling of a microfluidic device (and the micro fluidic elements within in it such as, e.g., microchannels, or pre-selected subsets of channels and/or other elements) as described above. Additionally, the use of "filling" or "fill" in a microfluidic device herein is used interchangeably with "pre-filling" to mean the filling of microfluidic elements, capillary elements, etc. with a gas and/or fluid during manufacture/preparation of the microfluidic device. It is to be appreciated that as used herein, the term "microfluidic device" incorporates the concept of a microfluidic device that comprises microfluidic elements such as, e.g., microfluidic channels (also called microchannels or microscale channels); therefore when a microfluidic device is described herein as being, e.g., evacuated or filled, it is to be understood that such microfluidic elements as are within such microfluidic device are also being evacuated or filled. The methods of the invention permit such filling to be done as to avoid unwanted trapped bubbles within the microfluidic channels or devices. The invention also provides systems and devices to perform the evacuating and filling of microfluidic channels and devices with desired gas(ses) and/or fluid(s). Such systems and devices allow control of, e.g., gas evacuation, submersion of evacuated microfluidic channels or devices under desired gas(ses)

and/or fluids, venting of the evacuated microfluidic channels and/or devices to the desired gas(ses) and/or fluids, and, e.g., optional detector systems and computer systems to monitor and control the evacuation/filling/etc. of the microfluidic channels and/or devices.

While the methods and devices of the current invention are especially applicable for microfluidic channels and/or microfluidic devices that are used in combination with capillary elements or that present intricate/complex channel configurations, they are equally useful for more 'simple' microfluidic channel configurations and/or microfluidic devices (i.e., ones without capillary elements or complex configurations). For example, depending upon the parameters of the specific uses (e.g., assays, etc.) of a microfluidic channel or device, in numerous applications, specific gas (ses) and/or fluids are desired in the fluidic elements of microfluidic devices. As one possible non-limiting example, some assays may need to be carried out in a high oxygen content environment, therefore, use of the methods and devices of the current invention can provide that the microfluidic elements and devices used in such assays can be filled with, e.g., a highly oxygenated fluid. Alternatively, in some situations, particular reactions, assays, etc. may need to avoid certain gasses, fluids, compounds, etc. Again, as a non-limiting example, some reactions need to be performed in anaerobic conditions. Use of the methods and devices of the current invention allow the used microfluidic elements and devices to be filled with, e.g., gas(ses) and/or fluids that are anaerobic.

Briefly, the methods and devices of the current invention involve evacuating and filling of microfluidic channels and/or devices in order to avoid bubbles trapped within the microfluidic channels and/or devices while at the same time minimizing filling time, allowing evacuation/filling of multiple microfluidic devices at the same time, and allowing for a wide range of possible gas(ses) and/or fluids to be used in the filling of the microfluidic channels and/or microfluidic devices. Other various methods and devices have previously been used to fill microfluidic channels and/or devices. For example, some previously used methods have involved such things as flowing a gas, e.g., carbon dioxide through each microfluidic device individually; allowing time for the carbon dioxide to saturate the microfluidic elements in the device; and then pulling a fluid, e.g., a sodium hydroxide solution, through the device which will dissolve and react with the carbon dioxide gas, thus wetting and filling the microfluidic elements of the device.

The current invention differs from the above methods and devices in numerous ways. For example, while other filling methods/systems, etc. have accomplished filling by, e.g., allowing desired gas(ses) to diffuse into microfluidic elements or devices followed by pulling a fluid through to react with the gas, the present invention accomplishes filling by first substantially evacuating the microfluidic elements and devices and then filling them with the desired gas(ses) and/or fluid(s). While previous methods dealt with bubbles trapped within the microfluidic elements and devices, e.g., by pressurizing then cooling the microfluidic elements/ devices, the current invention avoids trapped bubbles by first substantially evacuating all gas(ses) from the microfluidic elements and/or devices before filling them with the desired gas(ses) and/or fluid(s). Additionally, while other methods and devices accomplish filling of microfluidic elements or devices by, e.g., filling one microfluidic device at a time, the current methods and devices are flexible enough to allow multiple microfluidic elements and devices to be evacuated and filled simultaneously, thus allowing for savings in production costs, time usage, etc. Furthermore, since the methods and devices of the current invention rely on substantially evacuating all gasses from the microfluidic elements and devices before filling them with the desired gas(ses) and/or fluid(s) instead of relying on simple diffusion of, e.g., carbon dioxide into the areas of the microfluidic device, additional time saving is achieved.

The present invention also optionally includes various elements involved in, e.g., monitoring the evacuating and filling of microfluidic elements (e.g., microchannels) and microfluidic devices, temperature control, fluid transport mechanisms, robotic devices for, e.g., positioning of components or devices involved, etc.

METHODS AND DEVICES OF THE INVENTION

Microfluidic Devices to be Evacuated/Filled

The methods and devices of the invention involved in the evacuating and filling of microfluidic elements (e.g., microchannels, microreservoirs, etc.) are preferably done in relation to the filling of such microfluidic elements as comprising a microfluidic device. The term "microfluidic," as used herein, refers to a device component, e.g., chamber, channel, reservoir, or the like, that includes at least one cross-sectional dimension, such as depth, width, length, diameter, etc. of from about 0.1 micrometer to about 500 micrometer. Accordingly, the microfluidic devices, systems, elements, etc. evacuated/filled through use of the methods and/or devices of the present invention typically include at least one microscale channel, often at least two intersecting microscale channels, and often even three or more intersecting channels disposed within a single body structure. Such channels can intersect each other in a variety of ways, including, e.g., "T" intersection, off-set "T" intersections, "Y" intersections, cross intersections (i.e., "+"), or any number of other configurations wherein two or more channels are in fluid communication. Examples of microfluidic devices are detailed in, e.g., U.S. Pat. No. 5,942,443 issued Aug. 24, 1999, entitled "High Throughput Screening Assay Systems in Microscale Fluidic Devices" to J. Wallace Parce et al. and U.S. Pat. No. 5,880,071 issued Mar. 9, 1999, entitled "Electropipettor and Compensation Means for Electrophoretic Bias" to J. Wallace Parce et al., both of which are incorporated herein by reference for all purposes. In general, myriad different microscale systems, devices, and elements are optionally evacuated and filled through use of the methods and devices of the present invention.

Typically, microfluidic devices are planar in structure and are constructed from an aggregation of planar substrate layers wherein the fluidic elements, such as microchannels, etc., are defined by the interface of the various substrate layers. The microchannels, etc. are usually etched, embossed, molded, ablated or otherwise fabricated into a surface of a first substrate layer as grooves, depressions, or the like. A second substrate layer is subsequently overlaid on the first substrate layer and bonded to it in order to cover the grooves, etc. in the first layer, thus creating sealed fluidic components within the interior portion of the device. Additionally, microfluidic elements such as open-well microreservoirs, apertures, ports, etc. can be formed by creating perforations in one or more substrate layer, which perforation optionally can correspond to recessed areas on the opposing substrate layer and/or can be in communication with at least one of the, e.g., microchannels or microchambers within the microfluidic device. In the completed microfluidic device, such openings can function as reservoirs for allowing fluid and/or material introduction into the microfluidic elements (e.g., microchannels) of the interior areas of the microfluidic device and/or as channels of the microfluidic device to control and direct fluid transport within and through the device.

The substrate layers of microfluidic devices (including such ones as are filled by the methods and devices of the current invention) can be composed of numerous types of materials depending upon, e.g., the specific compounds, reagents, etc. to be assayed; the various procedures involved in the assays (such as how compounds are to be transported); and the substrate material's compatibility with known microfabrication techniques, e.g., photolithography, wet chemical etching, laser ablation, air abrasion techniques, injection molding, embossing, and other techniques. Substrate materials are typically chosen based upon their compatibility with the full range of conditions to which the microfluidic device may be exposed (e.g., ranges of pH, temperature, salt concentration, electric fields, etc.).

For example, the substrate layers of microfluidic devices, such as ones filled by the methods and devices of the current invention, can be composed of, e.g., metal materials; silica-based materials (such as glass, quartz, silicon, fused silica, or the like); polymeric materials (or a polymer coating on other materials) such as acrylics (e.g., polymethylmethacrylate), polycarbonate, polytetrafluoroethylene, polyvinylchloride, polydimethylsiloxane, polysulfone, polystyrene, polymethylpentene, polypropylene, polyethylene, polyvinylidine fluoride, acrylonitrile-butadiene-styrene copolymer, or the like; ceramic materials, etc. Also, depending upon the specific parameters of the desired use, specific areas of a microfluidic device can be lined with different substances than that substance of which the rest of the same microfluidic device is composed.

The surface of a substrate layer comprising a microfluidic device may be of the same material as the non-surface areas of the substrate or, alternatively, the surface may comprise a coating on the substrate base. Furthermore, if the surface is coated, the coating optionally can cover either the entire substrate base or can cover only select subparts of the substrate base, e.g., the surface of one or more microreservoir. For example, in the case of glass substrates, the surface of the glass of the base substrate may be treated to provide surface properties that are compatible and/or beneficial to one or more reagent used, etc. Such treatments include derivatization of the glass surface, e.g., through silanization or the like, or through coating of the surface using, e.g., a thin layer of other material such as a polymeric or metallic material. Derivatization using silane chemistry is well known to those of skill in the art and can be readily employed to add, e.g., amine, aldehyde, diol or other functional groups to the surface of the glass substrate, depending upon the desired surface properties. Alternatively, a glass layer may be provided as a coating over the surface of another base substrate, e.g., silicon, metal, ceramic, or the like.

In the case of polymer substrates, as with the glass or other silica based substrates described herein, the substrate may be comprised entirely of the polymer materials, or the polymer materials may be provided as a coating over a support element (i.e., base substrate). Such base substrates include, but are not limited to substances listed herein (e.g., metal, silicon, ceramic, glass, or other polymer or plastic card). In some cases, metal substrates are optionally used, either coated or uncoated, in order to take advantage of their conductivity.

Furthermore, in the case of metal substrates, metals that are not easily corroded under potentially high salt conditions, applied electric fields, and the like are optionally preferred. For this reason, titanium substrates, platinum substrates and gold substrates, for example, generally can be suitable, although other metals, e.g., aluminum, stainless steel, and the like, also can be useful.

Using the methods and devices of the present invention, appropriate gas(ses) and/or fluid(s) can be selected with which to fill microfluidic elements (e.g., microfluidic channels) and microfluidic devices. In addition to providing a way to avoid bubble formation in microfluidic elements (e.g., microchannels) and in microfluidic devices, the methods and devices of the invention can optionally be utilized to manipulate such things as assay parameters, etc. in the microfluidic elements and devices. The methods and devices herein can be accommodated to utilize gas(ses) and/or fluid(s) that specifically do not interact with the particular substrate material(s) (or substrate coating(s)) that comprise the microfluidic element or microfluidic device being evacuated/filled. Alternatively, the methods and devices herein can be accommodated to utilize gas(ses) and/or fluid(s) that specifically do interact with the particular substrate material(s) (or substrate coating(s)) that comprise the microfluidic element or microfluidic device being evacuated/filled. For example, a fluid 'A' that is used to fill an evacuated microfluidic device can optionally be chosen which interacts with substrate layer 'Y' (which lines or coats the microfluidic channels of the microfluidic device being filled). The interaction between 'A' and 'Y' can be one that, e.g., modifies the coatings/linings of the microfluidic channels of the device in order to, e.g., improve fluid flow through the microfluidic channels, etc.

Capillary Elements

Many microfluidic devices incorporate capillary elements (or other similar pipettor elements) such as sippers or electropipettors into their design. Such capillary elements are capable of sampling extremely small amounts of material and transporting the material into, e.g., a microfluidic channel(s) in the microfluidic device. The typical structure of one example of such a capillary element is illustrated in U.S. Pat. No. 5,779,868, issued Jul. 14, 1998, entitled "Electropipettor and Compensation Means for Electrophoretic Bias," issued to J. Wallace Parce et al. which is incorporated herein by reference in its entirety for all purposes. Microfluidic devices can include multiple capillary elements (e.g., 1, 2, 3, 4, 6, 8, 10, 12, 15, 20 or more elements) extending from the body of the microfluidic device.

In general, capillary elements incorporate at least one capillary channel that extends the length of the capillary element. One end of the capillary channel is typically opened while the opposing end of the channel is typically in fluid communication with at least one microfluidic element (e.g., a microchannel) within a microfluidic device. Material sampling is usually done by contacting the open end of the capillary channel with a source of a material to be analyzed, etc. Such material is then drawn into the capillary channel and thus transported into the microfluidic elements of the microfluidic device. Oftentimes the method of drawing the material into a capillary, as well as the transport of the material into the microfluidic elements of the device, is done via electrokinetic transport. In other words, an electric field is created between the material source and a point within the microfluidic device, thereby causing electrokinetic movement of the material into and through the capillary channel into the microfluidic device. Other methods of material sampling/transport are also optionally used, such as vacuum or pressure forces, wicking forces, etc.

Unfortunately, the incorporation of capillary elements in microfluidic devices can present problems in the wetting and filling of the microfluidic elements (e.g., microchannels) of the device. As stated previously, during the production and before their use in analyses, etc. microfluidic elements (such as microchannels) and microfluidic devices are typically and optionally wetted and filled with, e.g., a fluid such as, e.g., a buffer. Bubbles of air can often be trapped in the interface between a capillary element and the substrate layers of a microfluidic device during this wetting and filling. FIG. 1, shows a typical (but non-limiting) view of one possible configuration of a microfluidic device incorporating a capillary element while FIG. 2A, illustrates one possible non-limiting example of the interface between a capillary element and the substrate layers of a microfluidic device.

FIG. 1, panels A, B, and C provide additional details regarding an example microfluidic device that incorporates a capillary element. The device in FIG. 1 is one example of a microfluidic device that is capable of being evacuated/filled using the methods and devices of the current invention. During the microfluidic device's use, as shown, body structure 102 has a main channel 104 disposed therein. A sample or mixture of components, e.g., typically a buffer, is optionally flowed from capillary element 120 towards reservoir 114, e.g., by applying a vacuum at reservoir 114 (or another point in the system) or by, e.g., applying appropriate voltage gradients or wicking arrangements. Alternatively, a vacuum, or appropriate pressure force, is applied at, e.g., reservoirs 108, 112 or through capillary element 120. Additional materials, such as buffer solutions, substrate solutions, enzyme solutions, test molecules, fluorescence indicatory dyes and the like are optionally flowed from wells, e.g., 108 or 112 and into main channel 104. Flow from the microreservoir 114 is optionally performed, e.g., by modulating fluid pressure, by electrokinetic approaches, by wicking forces, by hydrostatic forces, etc. (or a combination of such forces, etc.). As fluid is added to main channel 104, e.g., from reservoir 108, the flow rate increases. The flow rate is optionally reduced by flowing a portion of the fluid from main channel 104 into flow reduction channel 106 or 110. The arrangement of channels depicted in FIG. 1 is only one possible arrangement out of many which are appropriate and available to be evacuated and filled using the methods and devices of the present invention. Additional alternatives can be readily devised, e.g., by combining microfluidic elements such as flow reduction channels, with other microfluidic devices in the patents and applications referenced herein. Also, optional configurations can include, e.g., a variable number of capillary elements integrated into the microfluidic device. Such optional configurations incorporating multiple capillary elements can also optionally be evacuated and filled by the methods and devices of the invention.

The microfluidic devices which are capable of being evacuated and filled by the invention typically include at least one main analysis channel, but may include two or more main analysis channels in order to multiplex the number of analyses being carried out in the microfluidic device at any given time. Typically, a single microfluidic device will include from about 1 to about 100 or more separate analysis channels. In most cases, the analysis channel is intersected by at least one other microscale channel disposed within the body of the device. Typically, the one or more additional channels are used, e.g., to bring the samples, test compounds, assays reagents, etc. into the main analysis channel, in order to carry out the desired analysis. Additionally, the width of the microfluidic channels can optionally be wider in some microfluidic devices than in other microfluidic devices depending upon the desired use of the device.

Figure 2A:
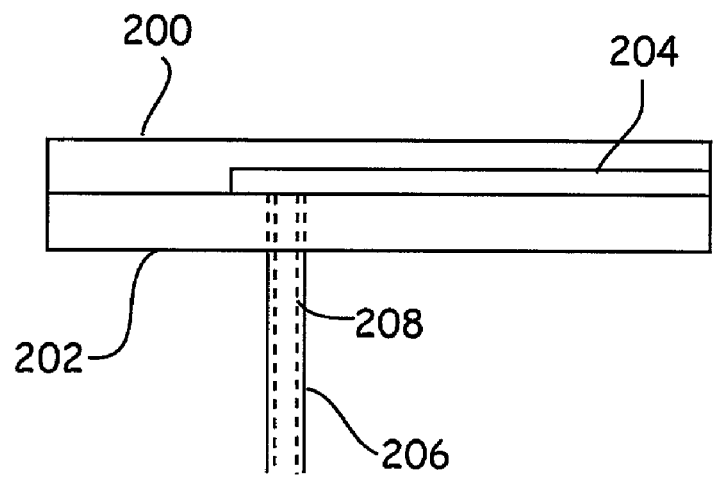
FIG. 2, panel A is a schematic side view of the junction between a capillary element and a microfluidic device; panel B is a schematic view of complex/intricate microchannel configuration.

FIG. 2A illustrates one possible arrangement of the interface between a capillary element and a microfluidic element in a microfluidic device. One will appreciate that the illustrated arrangement is not limiting and that numerous other possible interactions between microfluidic elements (e.g., in microfluidic devices) and capillary elements are possible. As stated, supra, microfluidic devices (and thus the microfluidic elements, such as microchannels, incorporated within them, such as microchannels) are wetted and filled before use in analyses. The wetting and filling of an interface between a capillary element and a microfluidic device, as is shown in FIG. 2A, can be problematic in that bubbles can become trapped within the interface. Such bubbles can often severely interfere with any analysis later done involving the microfluidic element or microfluidic device containing such bubbles. Obviously, in microfluidic devices containing multiple capillary elements, the bubble problem is magnified (see, e.g., FIG. 4, below). As shown in FIG. 2A, substrate layers 200 and 202 enclose and define microfluidic element (here a microfluidic channel) 204. Capillary element 206, travels through substrate layer 202 and opens into microfluidic channel 204. Capillary element 206 contains within it, capillary lumen 208. In a microfluidic device such as illustrated in FIG. 2A, fluid(s) and/or material(s) are drawn up through capillary element 206 and into microfluidic channel 204. During the initial wetting and filling of the microfluidic device (e.g., done at time of preparation/manufacture before the device is used for analysis, etc.) air bubbles can be trapped in the juncture between capillary element 206 and the substrate layers 200 and 202 which define microfluidic channel 204.

Figure 2B:
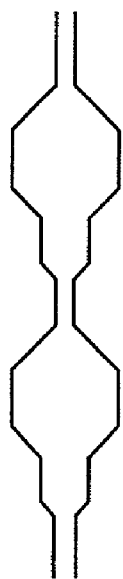

FIG. 2B illustrates one possible configuration of an intricate/complex microfluidic channel cross-sectional profile. It will be appreciated that the configuration shown is only one such possible cross-sectional profile and that numerous other arrangements are possible. The wetting and filling of a complex/intricate microchannel cross-sectional profile as is shown in FIG. 2B can result in trapped bubbles. As shown in FIG. 2B, microchannel area 212 is much narrower in comparison to microchannel area 214. If filling of such a microchannel is done using current wetting/filling techniques (e.g., pushing or pulling fluids through a microfluidic device), then initial wetting and filling of such a microchannel can leave bubbles trapped in slower flowing (or "eddy") areas, e.g., against the outer walls of the microchannel in its broader sections such as 214.

Figure 4:
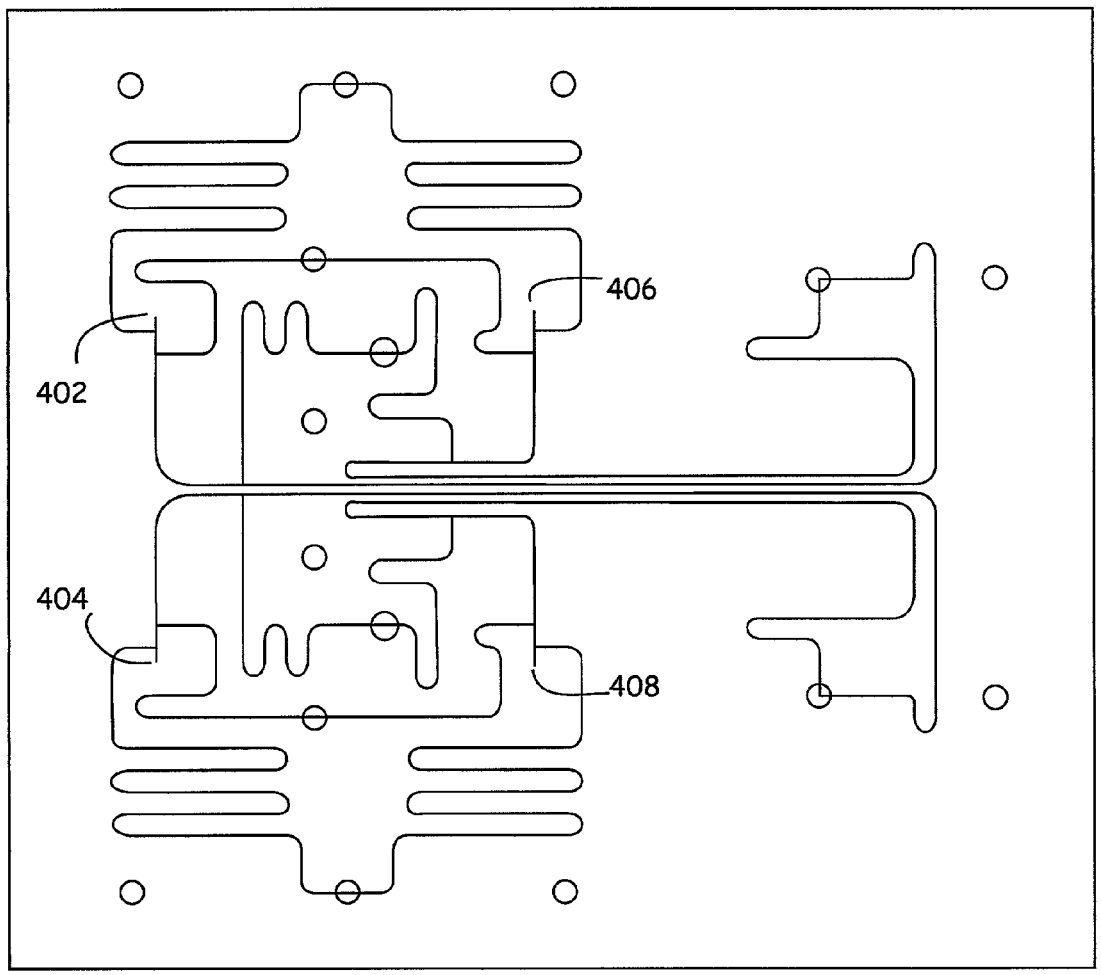
FIG. 4 is a schematic diagram (top view) of an example microfluidic device (including four capillary elements and a complex channel arrangement) capable of being evacuated and filled through use of the methods and devices of the invention.

FIG. 4 illustrates an additional possible arrangement of a microfluidic device capable of being evacuated and filled using the methods and devices of the invention. FIG. 4 shows one example of a more "complex" microfluidic device arrangement, e.g., one having, e.g., varying channel cross-sectional areas, complex dimension networks, etc., that is capable of being evacuated/filled using the methods and devices of the present invention. As shown in FIG. 4, the microfluidic device incorporates 4 capillary elements, 402, 404, 406, and 408, as seen in top view. As described above, such a microfluidic device poses areas of concern in wetting and filling. For example, areas where capillary elements 402, 404, 406, and 408 join with the body of the microfluidic device, unwanted bubbles may become trapped during the wetting and filling of the device. However, the methods and devices of the present invention avoid such bubbles through the evacuation, etc. of the microfluidic device as described herein. Also, as illustrated in FIG. 4, the microfluidic device shown has a number of intricate channel configurations which if using other means of wetting and filling the device, could require longer time periods to allow a gas, e.g., carbon dioxide, to diffuse into all areas. Again, the methods and devices of the present invention, avoid such diffusion time requirements because the device is evacuated/filled, etc. as described herein.

Examples of uses of the Methods and Devices of the invention

As outlined previously, microfluidic devices are typically filled with a gas, or more often, a fluid before they are used to perform desired analyses, etc. This filling, or more typically wetting and filling, is generally done at time of preparation or manufacture of the microfluidic device. Such wetting and filling is done for numerous purposes, such as allowing modification of the surfaces of various microfluidic elements (e.g., microchannels) within a microfluidic device, avoidance of bubble formation which might occur when fluids are drawn through an empty microfluidic device, etc. Additionally, some fluids used to wet and fill microfluidic devices can optionally act as preservatives to prevent contamination of the fluidic areas within a microfluidic device. For example, to such an end, solutions of, e.g., ethylene-diamine-tetra-acetic acid (EDTA) can optionally be used as a filling fluid.

Currently, one primary way to accomplish wetting and filling of microfluidic devices (especially ones incorporating capillary elements) is to distribute carbon dioxide through each microfluidic device to be wetted and filled. Carbon dioxide is flowed into a microfluidic device and allowed to diffuse into all areas. Diffusion into areas is especially important in regions/areas where flow of carbon dioxide is not an option (e.g., "dead-leg areas" areas, e.g., microchannels, having no end outlet, such as "T" formations). Such actions are usually done to each microfluidic device singularly. The carbon dioxide is allowed to fully saturate the microfluidic elements of the device (i.e., to permeate through all microchannels, capillary elements, etc.). The time required for the carbon dioxide to diffuse through all of the elements of the microfluidic device depends upon several factors including, e.g., the size, complexity and number of the microfluidic elements involved in the device (i.e., greater complexity, etc. can require a greater diffusing time for the carbon dioxide). Once the carbon dioxide is diffused throughout the elements of the microfluidic device, a solution of sodium hydroxide is pulled through the microfluidic device. As the sodium hydroxide solution is pulled through the device, the carbon dioxide dissolves into, and reacts with, the solution, thus wetting and filling the fluidic elements of the microfluidic device (e.g., the various microchannels, etc. within the microfluidic device). Other techniques involve simply pushing or pulling fluid through the microfluidic elements of a microfluidic device (i.e., using pressure or vacuum respectively).

Unfortunately, the above methods often leave bubbles trapped at the interface between capillary elements and the microfluidic element (e.g., microchannel) into which the capillary element flows. Bubble formation may also be problematic in certain microchannel configurations. This is especially true if the width of a microchannel greatly increases or decreases within a short distance. In such situations, areas of gas may be trapped in eddies by the sides of the microchannels and out of the higher flow center area of the microchannel. If bubbles do get trapped within a microfluidic device using the above technique, then one possible method used to clear the bubbles involves pressurizing, then cooling, the microfluidic device. The purpose of such steps is to attempt to force dissolution of the trapped bubbles into the fluid in the microfluidic elements (e.g., microchannels) of the device.

The methods and devices of the current invention accomplish wetting and filling of microfluidic elements (e.g., microchannels) of microfluidic devices while avoiding trapping gas bubbles within the microfluidic devices. In the methods of the current invention, a microfluidic element (generally a microfluidic channel, but also other elements such as, but not limited to, microreservoirs, microchambers, etc.) is evacuated by being placed under a total or partial vacuum and filled with a desired gas and/or fluid. In preferred embodiments, the microfluidic elements are incorporated in a microfluidic device.

Figure 3:
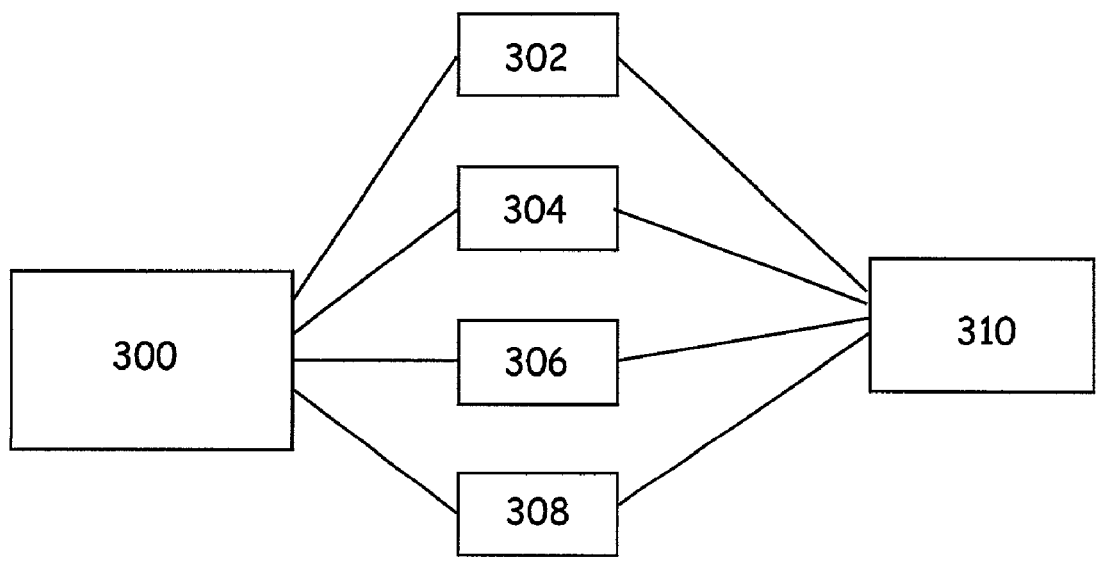
FIG. 3 is a schematic diagram of an example arrangement of the devices of the invention.

The diagram, FIG. 3, illustrates one possible configuration of the devices of the invention. It will be appreciated that the configuration shown in FIG. 3 can be optionally modified while staying within the scope of the methods and devices of the invention. As illustrated in FIG. 3, chamber 300 is used to hold one or more microfluidic devices, depending upon the size of the microfluidic devices and of the chamber. Once the appropriate microfluidic devices are placed within vacuum chamber 300, the chamber is sealed and the contents of the chamber (i.e., the one or more microfluidic devices) are placed under total or partial vacuum. In various embodiments of the invention, the level of vacuum under which the chamber (and hence the contents of microfluidic device(s)) is placed can range from between about 0.5 and about 102 kPa, from between about 15 and about 85 kPa, from between about 30 and about 70 kPa, from between about 45 and about 55 kPa, or more preferably from between about 0.5 and about 5 kPa. The vacuum is created by, e.g., using a vacuum source such as vacuum source 302 in FIG. 3. Vacuum sources are well known in the art and numerous ones (e.g., involving pumps, etc.) are commercially available. By placing the microfluidic devices in the chamber under total or partial vacuum, the microfluidic elements within the microfluidic devices become substantially evacuated (i.e., the gasses within the microfluidic elements (such as the microchannels) is drawn out of the elements and out of the microfluidic device).

After the microfluidic devices in vacuum chamber 300, are placed under a total or partial vacuum, the next step in filling the microfluidic devices comprises submerging the substantially evacuated microfluidic devices in a gas or a degassed fluid. For fluid filling of microfluidic devices, as described herein, degassed fluids are most preferred because of the desire to avoid gas evolution during filling or generation of the device, which can lead to, e.g., unwanted bubble formation. As shown in FIG. 3, gas/fluid source 304 admits the gas and/or fluid into substantially evacuated chamber 300 which contains the one or more microfluidic device. The construction of the source(s) of the gas(ses) and/or fluid(s) inserted into the vacuum chamber is optionally dependent upon the nature of the fluid(s) and/or gas(ses) involved (i.e., the gas/fluid source is optionally configured (for such things are injection styles, methods, holding facilities, etc.) for each type of gas/fluid to be inserted. The gas and/or fluid under which the substantially evacuated microfluidic devices are submerged can be any of a number of materials including, but not limited to buffers, water, EDTA solutions, carbon dioxide, nitrogen, etc. (see, supra). Additionally, combinations of both gas and fluid can be used to submerge the substantially evacuated microfluidic devices.

After being submerged under the appropriate gas(ses) and/or fluid(s) the substantially evacuated microfluidic devices are optionally vented to the gas and/or fluid under which they are submerged. Since the gas(ses) and fluid(s) are at a higher pressure than the interior elements of the substantially evacuated microfluidic devices, the gas(ses) and/or fluid(s) move in to fill the total or partial vacuum within the microfluidic elements, thereby filling the microfluidic devices. Furthermore, the methods and devices of the invention permit sequential additions of selected gas(ses) and/or fluids(s). For example, a substantially evacuated microfluidic device can optionally be submerged under, e.g., a selected gas followed by submersion under a selected fluid, which fluid optionally can diffuse into and/or react with the gas. It will be appreciated that during or after the submerged microfluidic devices are vented to the gasses/liquids within the chamber, the internal pressure of the chamber can optionally be increased to, e.g., atmospheric pressure, less than atmospheric pressure, or greater than atmospheric pressure (or a sequential combination of such pressures), without the chamber being opened to or exposed to ambient atmosphere. It will also be appreciated that venting of submerged microfluidic devices is optionally also done to ambient atmosphere in desired applications, as opposed to and/or in addition to the venting of microfluidic devices to the gasses/fluids within the chamber (as outlined above).

One possible optional embodiment of the devices of the invention comprises wherein a venting system controls the venting of the submerged microfluidic devices to the gas(ses) and/or fluid(s) in which they are submerged. As shown in FIG. 3, optional venting system 306 can manipulate the venting of submerged microfluidic devices to the surrounding gasses and/or fluids. Alternatively, instead of a venting system, the gas(ses) and/or fluid(s) added to the substantially evacuated chamber (300 in FIG. 3) from gas/fluid source 304 can both submerge and fill the microfluidic devices at the same time. In other words, since the pressure of the gas/fluid is higher than the total or partial vacuum in the microfluidic elements of the microfluidic devices in Chamber 300, the gas/fluid will move to fill the vacuum within the microfluidic devices thereby filling them. In such an embodiment the submerging and venting steps (as given above) are basically combined into one submerging-venting step.

Optional embodiments of the devices of the invention can include but are not limited to optional configurations involving, e.g., monitors/detectors, computer systems, etc. As shown in FIG. 3, optional Detector/Monitor 308 can be used to track the various evacuation and filling events, etc. performed by the devices of the invention.

In general, detection systems which optionally can be included in the devices of the invention include, but are not limited to, such things as optical sensors, fluid level sensors, temperature sensors, pressure sensors, conductivity sensors, and the like. Each of these types of sensors is readily incorporated into the devices described herein. In these systems, such detectors are placed either within or adjacent to the vacuum chamber holding the microfluidic devices to be evacuated and filled (e.g., Chamber 300 in FIG. 3) such that the detector is within sensory communication with the device, chamber, etc. The phrase "proximal," to a particular element or region, as used herein, generally refers to the placement of the detector in a position such that the detector is capable of detecting the property of the devices of the invention, a portion of such device, or the contents of a portion of such device, for which that detector was intended. For example, a pressure sensor placed in sensory communication with a vacuum chamber such as Chamber 300 in FIG. 3 is capable of determining the level of pressure/vacuum which exists in that chamber. A fluid level sensor (e.g., a float, optical detector, etc.) is capable of determining the level of fluid (e.g., degassed fluid) in, e.g., a vacuum chamber. Similarly, a temperature sensor placed in sensory communication with the body of a vacuum chamber is capable of determining the temperature of such a device itself.

Examples of optional detection systems in the current invention can include, e.g., optical detection systems for detecting an optical property of a material within, e.g., the microchannels of a microfluidic device contained within, e.g., a vacuum chamber of a device of the invention as described herein. Such optical detection systems are typically placed adjacent to a microscale channel of a microfluidic device, and optionally are in sensory communication with the channel via an optical detection window or zone that is disposed across the channel or chamber of the device. Such an optional optical detection system can be used in the devices of the invention to, e.g., monitor the evacuation and/or filling of the microfluidic elements of microfluidic devices (e.g., to detect that all areas, or a subset of areas (e.g., problematic microchannel areas such as "dead-legs" (see above)) are filled with the desired gas(ses) and/or fluid(s))within, e.g., a vacuum chamber such as Chamber 300 as shown in FIG. 3.

Optional optical detection systems of the invention include, e.g., systems that are capable of measuring the light emitted from material within a channel, the transmissivity or absorbance of the material, as well as the material's spectral characteristics, e.g., fluorescence, chemiluminescence. Detectors optionally detect a labeled compound, such as fluorographic, colorimetric and radioactive components. Types of detectors optionally include spectrophotometers, photodiodes, avalanche photodiodes, microscopes, scintillation counters, cameras, diode arrays, imaging systems, photomultiplier tubes, CCD arrays, scanning detectors, galvo-scanners, film and the like, as well as combinations thereof. Examples of suitable detectors are widely available from a variety of commercial sources known to persons of skill. See, also, *The Photonics Design and Application Handbook*, books 1, 2, 3 and 4, published annually by Laurin Publishing Co., Berkshire Common, P.O. Box 1146, Pittsfield, Mass. for common sources for optical components.

As noted above, microfluidic devices such as ones capable of being evacuated and/or filled by the present devices typically include a detection window or zone at which a signal, e.g., fluorescence, is monitored. Such a detection window or zone also typically includes a transparent cover allowing visual or optical observation and detection of the evacuation/filling results, e.g., observation of a colorimetric, fluorometric or radioactive response.

The optional sensor or detection portion of the devices and methods of the present invention can optionally comprise a number of different apparatuses. For example, fluorescence (if such is used to monitor the evacuation/filling of microfluidic devices within the devices of the present invention) can be detected by, e.g., a photomultiplier tube, a charge coupled device (CCD) (or a CCD camera), a photodiode, or the like. Such apparatuses are commonly used in many laboratory applications and settings and are well known to those in the art.

In some aspects, the optional detector can measure an amount of light emitted from a material, such as a fluorescent or chemiluminescent material. As such, the optional detection system will typically include collection optics for gathering a light based signal and transmitting that signal to an appropriate light detector. Microscope objectives of varying power, field diameter, and focal length are readily utilized as at least a portion of this optical train. The optional detection system is typically coupled to a computer (described in greater detail below), via an analog to digital or digital to analog converter, for transmitting detected light data to the computer for analysis, storage and data manipulation.

In some situations, the optional detector can include a light source which produces light at an appropriate wavelength for activating a fluorescent material, as well as optics for directing the light source to the material contained in, e.g., a microfluidic device within the devices of the invention. The light source can be any number of light sources that provides an appropriate wavelength, including lasers, laser diodes and LEDs. Typically, light selection parameters are well known to those of skill in the art.

The optional detector can exist as a separate unit, but is preferably integrated with the other components, into a single instrument. Integration of these functions into a single unit facilitates connection of these instruments with a computer (described below), by permitting the use of few or a single communication port(s) for transmitting information between, e.g., the vacuum chamber, the detector and the computer. Integration of the detection system with a computer system typically includes software for converting detector signal information into assay result information, e.g., internal pressure in a vacuum chamber, degree of evacuation in microfluidic elements of microfluidic devices contained within a vacuum chamber of the invention, or the like.

Computer

As noted above, any, all, or any combination of, e.g., the vacuum source, gas/fluid addition system, venting system, etc. as well as other aspects of the current invention described herein optionally can be coupled to an appropriately programmed processor or computer that functions to instruct the operation of these instruments in accordance with preprogrammed or user input instructions, receive data and information from these instruments, and interpret, manipulate and report this information to the user. As such, the computer is typically appropriately coupled to one or more of the appropriate instruments (e.g., including an analog to digital or digital to analog converter as needed). Again, FIG. 3, displays a schematic diagram indicating one possible arrangement of one possible embodiment of the devices of the invention. As shown in FIG. 3, computer 310, is operably (and optionally) coupled to, e.g., vacuum source 302, gas/fluid addition system 304, venting system 306, etc. Of course, the devices of the invention are flexible enough so as to carry out the methods, purposes, etc. of the invention without the incorporation of an optional computer system.

The computer optionally includes appropriate software for receiving user instructions, either in the form of user input into set parameter fields, e.g., in a GUI, or in the form of preprogrammed instructions, e.g., preprogrammed for a variety of different specific operations. The software then converts these instructions to appropriate language for instructing the operation of, e.g., application of a total or partial vacuum to chamber 300 (as shown in FIG. 3), etc. to carry out the desired operation.

For example, the computer is optionally used to direct a gas/fluid addition system (e.g., 302 in FIG. 3) to control gas/fluid flow, e.g., into and through the vacuum chamber (e.g., 300 in FIG. 3). Additionally, the optional computer system optionally directs, e.g., evacuation of gasses from the vacuum chamber. Furthermore, the optional computer system optionally controls the coordination of movements of multiple fluids/molecules/etc. concurrently as well as sequentially. For example, the computer optionally directs the gas/fluid addition system to, e.g., add first a selected gas, then a selected fluid to the vacuum chamber containing the microfluidic devices to be evacuated and filled by the methods and devices of the invention.

The computer also optionally receives data from the one or more sensors/detectors included within the system, interprets the data, and either provides it in a user understood format, or uses that data to initiate further controller instructions, in accordance with the programming, e.g., such as in monitoring and control of flow rates (e.g., as involved in adding gas/fluid to the vacuum chamber, etc.), temperatures, applied voltages, pressures, and the like.

In the present invention, the computer typically includes software for the monitoring and control of materials in the various aspects of the device, etc. For example, the software directs flow switching to control and direct gas/fluid flow as described above. Additionally the software is optionally used to control electrokinetic, pressure-modulated, or the like, injection or withdrawal of material. The injection or withdrawal is optionally used to modulate the flow rate as described above.

In addition, the computer optionally includes software for deconvolution of the signal or signals from, e.g., a detection system. For example, the deconvolution distinguishes the degree of evacuation from within microfluidic elements of microfluidic devices within a vacuum chamber of the device of the invention.

Any controller or computer optionally includes a monitor which is often a cathode ray tube ("CRT") display, a flat panel display (e.g., active matrix liquid crystal display, liquid crystal display), or the like. Data produced from the device, e.g., withdrawal of gasses from the vacuum chamber, is optionally displayed in electronic form on the monitor. Additionally, the data gathered from the device can be outputted in printed form. The data, whether in printed form or electronic form (e.g., as displayed on a monitor), can be in various or multiple formats, e.g., curves, histograms, numeric series, tables, graphs and the like.

Computer circuitry is often placed in a box which includes, e.g., numerous integrated circuit chips, such as a microprocessor, memory, interface circuits, etc. The box also optionally includes such things as a hard disk drive, a floppy disk drive, a high capacity removable drive such as a writeable CD-ROM, and other common peripheral elements. Inputting devices such as a keyboard or mouse optionally provide for input from a user and for user selection of sequences to be compared or otherwise manipulated in the relevant computer system.

Filling/Prep Kits

The present invention also provides kits for utilizing the methods and devices of the invention. In particular, these kits typically include evacuation/filling devices, systems, modules and workstations (e.g., vacuum chambers, gas/fluid addition systems, etc.) for performing the evacuation/filling, etc. of the invention. A kit optionally contains additional components for the assembly and/or operation of a multi-module workstation of the invention including, but not restricted to robotic elements (e.g., a track robot, a robotic armature, or the like), plate handling devices, fluid handling devices, and computers (including e.g., input devices, monitors, C.P.U., and the like).

Generally, the evacuation/filling devices described herein are optionally packaged to include some or all reagents for performing the device's functions (e.g., gas/fluids, etc. to be used in filling microfluidic devices). For example, the kits can optionally include any of the devices described herein, along with assay components, buffers, reagents, sample materials, substrates, control material, spacers, buffers, immiscible fluids, etc., (e.g., to be used in filling of microfluidic devices) for performing the evacuation/filling actions of the invention. In the case of prepackaged reagents, the kits optionally include pre-measured or pre-dosed reagents that are ready to incorporate into the methods of the invention without measurement, e.g., pre-measured fluid aliquots used to fill various devices/chambers (e.g., a vacuum chamber of the invention), etc., or pre-weighed or pre-measured solid reagents that can be easily reconstituted by the end-user of the kit.

Such kits also typically include appropriate instructions for using the above devices and reagents, and in cases where reagents (or all necessary reagents) are not predisposed in the devices themselves, with appropriate instructions for introducing the reagents into the, e.g., vacuum chambers, gas/fluid addition systems, etc. of the device. In this latter case, these kits optionally include special ancillary devices for introducing materials into, e.g., the gas/fluid addition system 304, the main chamber 300, etc. Appropriate ancillary devices include such things as, e.g., appropriately configured syringes/pumps, or the like. Additionally, these kits optionally include special ancillary devices for withdrawing material, e.g., withdrawing unwanted and/or excess gas/fluid from a vacuum chamber, etc. Generally, such reagents, materials, etc. are provided in a stabilized form, so as to prevent degradation or other loss during prolonged storage, e.g., from leakage. A number of stabilizing processes are widely used for reagents that are to be stored, such as the inclusion of chemical stabilizers (i.e., enzymatic inhibitors, microbicides/bacteriostats, anticoagulants), the physical stabilization of the material, e.g., through immobilization on a solid support, entrapment in a matrix (i.e., a bead, a gel, etc.), lyophilization, or the like.

The elements of the kits of the present invention are typically packaged together in a single package or set of related packages. The package optionally includes written instructions for utilizing one or more device of the invention in accordance with the methods described herein. Kits also optionally include packaging materials or containers for holding the evacuation/filling device, system or reagent elements.

The discussion above is generally applicable to the aspects and embodiments of the invention described herein. Moreover, modifications are optionally made to the methods and devices described herein without departing from the spirit and scope of the invention as claimed, and the invention is optionally put to a number of different uses.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A method of filling at least one microfluidic element of a microfluidic device with a gas or fluid, the method comprising:
    placing the microfluidic device in a vacuum chamber;
    applying a vacuum to the vacuum chamber;
    while the microfluidic device remains under vacuum, introducing the gas or fluid into the vacuum chamber such that the microfluidic device is submerged in to gas or fluid;
    venting the at least one microfluidic element to the gas or fluid; and
    filling the at least one microfluidic element with the gas or fluid.

2. The method of claim 1 wherein applying a vacuum comprises applying a vacuum between about 0.5 and 102 kPa.

3. The method of claim 1 wherein applying a vacuum comprises applying a vacuum between about 15 and 85 kPa.

4. The method of claim 1 wherein applying a vacuum comprises applying a vacuum between about 30 and 70 kPa.

5. The method of claim 1 wherein applying a vacuum comprises applying a vacuum between about 45 and 55 kPa.

6. The method of claim 1 wherein applying a vacuum comprises applying a vacuum between about 0.5 and 5 kPa.

7. The method of claim 1 wherein filling the at least one microfluidic element with the gas or fluid comprises filling the at least one microfluidic channel with a degassed fluid.

8. The method of claim 1 wherein filling the at least one microfluidic element with the gas or fluid comprises filling the at least one microfluidic element with at least one fluid selected from a group consisting of water, buffer, EDTA solution, DMSO, PEG, polyacrylamide, and NaOH solution.

9. The method of claim 1 wherein filling the at least one microfluidic element with the gas or fluid comprises diffusing the gas or fluid into the at least one microfluidic element.

10. The method of claim 1 wherein the at least one microfluidic element is fluidly connected to an at least one capillary element, which element includes a capillary channel disposed therein.

11. The method of claim 1 wherein the at least one microfluidic element comprises a plurality of microfluidic channels.

12. The method of claim 11 wherein the plurality of microfluidic channels are fluidly coupled to one or more micro-reservoirs.

13. The method of claim 1 wherein filling the at least one microfluidic element with the gas or fluid comprises filling the at least one microfluidic element with at least one inert gas.

14. The method of claim 13 wherein the at least one inert gas is selected from a group consisting of carbon dioxide and nitrogen.

15. The method of claim 1 wherein filling the at least one microfluidic element with the gas or fluid comprises filling the at least one microfluidic element with both a gas and a fluid.

16. A system for filling a microfluidic element of a microfluidic device with a gas or a fluid, the system comprising:
    a) a chamber configured to receive the microfluidic device;
    b) a vacuum source which is fluidly coupled to the chamber and which is configured to apply a vacuum to the chamber;

c) at least one source of a gas or fluid which is fluidly coupled to the chamber and which is configured to introduce at least one of a gas or a fluid into the chamber; and d) a detector configured to monitor filling of the microfluidic element of the microfluidic device with the gas or fluid.

17. The system of claim 16 wherein the microfluidic element comprises at least one microfluidic channel.

18. The system of claim 16 wherein the vacuum source is applicable to apply a vacuum between about 0.5 and 102 kPa to the chamber.

19. The system of claim 16 wherein the vacuum source is applicable to apply a vacuum between about 15 and 85 kPa to the chamber.

20. The system of claim 16 wherein the vacuum source is applicable to apply a vacuum between about 30 and 70 kPa to the chamber.

21. The system of claim 16 wherein the vacuum source is applicable to apply a vacuum between about 0.5 and 5 kPa to the chamber.

22. The system of claim 16 further comprising a processor operably coupled to the microfluidic device, wherein the processor comprises an instruction set for acquiring data from the detector and for controlling filling of the microfluidic device with the gas or the fluid.

* * * * *